US008435768B2

(12) United States Patent
Sineoky et al.

(10) Patent No.: US 8,435,768 B2
(45) Date of Patent: May 7, 2013

(54) **METHOD FOR PRODUCING SUCCINIC ACID USING A YEAST BELONGING TO THE GENUS *YARROWIA***

(75) Inventors: Sergay Pavlovich Sineoky, Moscow (RU); Tigran Vladimirovich Yuzbashev, Moscow (RU); Evgenia Yurievna Yuzbasheva, Moscow region (RU); Tatyana Ivanovna Sobolevskaya, Udmurtskaya republic (RU); Ivan Aleksandrovich Laptev, Moscow (RU); Tatyana Vladimirovna Vibornaya, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/186,937

(22) Filed: Jul. 20, 2011

(65) Prior Publication Data

US 2012/0015415 A1 Jan. 19, 2012

Related U.S. Application Data

(63) Continuation of application No. PCT/JP2010/051463, filed on Jan. 27, 2010.

(30) Foreign Application Priority Data

Jan. 30, 2009 (RU) ................ 2009103058

(51) Int. Cl.
*C12P 7/46* (2006.01)
*C12N 1/19* (2006.01)
*C12N 1/16* (2006.01)

(52) U.S. Cl.
USPC ............ 435/145; 435/254.2; 435/255.1

(58) Field of Classification Search .................. None
See application file for complete search history.

(56) References Cited

U.S. PATENT DOCUMENTS

| | | | |
|---|---|---|---|
| 6,159,738 A | 12/2000 | Donnelly et al. | |
| 2003/0017559 A1 | 1/2003 | Donnelly et al. | |
| 2005/0192426 A1* | 9/2005 | Swift et al. ............ | 528/328 |
| 2006/0046288 A1 | 3/2006 | Ka-Yiu et al. | |
| 2007/0042476 A1 | 2/2007 | Lee et al. | |
| 2007/0042477 A1 | 2/2007 | Lee et al. | |
| 2007/0111294 A1 | 5/2007 | Burgard et al. | |
| 2008/0020436 A1 | 1/2008 | Lee et al. | |

FOREIGN PATENT DOCUMENTS

| | | |
|---|---|---|
| JP | 2001-103958 | 4/2001 |
| WO | WO2008/128522 | 10/2008 |
| WO | WO2009/011974 | 1/2009 |
| WO | WO2009/065778 | 5/2009 |
| WO | WO2010/037111 | 4/2010 |

OTHER PUBLICATIONS

Kubo et al (Effect of gene disruption of succinate dehydrogenase on succinate production in a sake yeast strain (Journal of Bioscience and Bioengineering vol. 90, issue 6, 2000, p. 619-624.*

Jean-Marie Backerich, *Yarrowia lipolitica*: a model organism for protein secretion studies Internatl Microbiol (1998) 1:123-130.*
Kubo, Y., et al., "Effect of Gene Disruption of Succinate Dehydrogenase on Succinate Production in a Sake Yeast Strain," J. Biosci. Bioeng. 2000;90(6):619-624.
Lin, H., et al., "Chemostat culture characterization of *Escherichia coli* mutant strains metabolically engineered for aerobic succinate production: A study of the modified metabolic network based on metabolite profile, enzyme activity, and gene expression profile," Metabol. Eng. 2005;7:337-352.
International Search Report and Written Opinion for PCT Patent App. No. PCT/JP2010/051463 (May 17, 2010).
Ahlers, S. E., et al., "Effects of a Temperature-Sensitive Mutation in the Immediate-Early Gene of Pseudorabies Virus on Class II and Class III Gene Transcription," J. Virol. 1987;61(4):1103-1107.
Arikawa, Y., et al., "Effect of Gene Disruptions of the TCA Cycle on Production of Succinic Acid in *Saccharomyces cerevisae*," J. Biosci. Bioeng. 1999;87(1):28-36.
Il'Chenko, A. P., et al., "Metabolism of *Yarrowia lipolytica* Grown on Ethanol under Conditions Promoting the Production of α-Ketoglutaric and Citric Acids: A Comparative Study of the Central Metabolism Enzymes," Microbiol. 2002;71(3):269-274.
Kamzolova, S. V., et al., "Oxygen requirements for growth and citric acid production of *Yarrowia lipolytica*," Fems Yeast Res. 2003;3:217-222.
Kamzolova, S. V., et al., "Chemically assisted microbial production of succinic acid by the yeast *Yarrowia lipolytica* grown on ethanol," Appl. Microbiol. Biotechnol. 2009;83:1027-1034.
Lee, S. J., et al., "Genome-Based Metabolic Engineering of *Mannheimia succiniciproducens* for Succinic Acid Production," Appl. Environmen. Microbiol. 2006;72(3):1939-1948.
Lin, H., et al., "Genetic Reconstruction of the Aerobic Central Metabolism in *Escherichia coli* for the Absolute Aerobic Production of Succinate," Biotechnol. Bioeng. 2005;89(2):148-156.
Lin, H., et al., "Fed-Batch Culture of a Metabolically Engineered *Escherichia coli* Strain Designed for High-Level Succinate Production and Yield Under Aerobic Conditions," Biotechnol. Bioeng. 2005;90(6):775-779.
McKinlay, J. B., et al., "Insights into *Actinobacillus succinogenes* Fermentative Metabolism in a Chemically Defined Growth Medium," Appl. Environmen. Microbiol. 2005;71(11):6651-6656.
Samuelov, N. S., et al., "Influence of $CO_2$-$HCO_3^-$ Levels and pH on Growth, Succinate Production, and Enzyme Activities of *Anaerobiospirillunt succiniciproducens*," Appl. Environmen. Microbiol. 1991;57 (10): 3013 -3019.
Wu, H., et al., "Improved Succinic Acid Production in the Anaerobic Culture of an *Escherichia coli pflB ldhA* Double Mutant as a Result of Enhanced Anaplerotic Activities in the Preceding Aerobic Culture," Appl. Environmen. Microbiol. 2007;73 (24):7837 -7843.
Arikawa, Y., et al., "Effect of Gene Disruptions of the TCA Cycle on Production of Succinic Acid in *Saccharomyces cerevisiae*," J. Biosci. Bioeng. 1999;87(1):28-36.

* cited by examiner

*Primary Examiner* — Kagnew H Gebreyesus
(74) *Attorney, Agent, or Firm* — Shelly Guest Cermak; Cermak Nakajima LLP

(57) ABSTRACT

The present invention provides a method for producing succinic acid using a yeast belonging to the genus *Yarrowia*, which has been modified to reduce activity of succinate dehydrogenase in said yeast.

7 Claims, 2 Drawing Sheets

METHOD FOR PRODUCING SUCCINIC ACID USING A YEAST BELONGING TO THE GENUS YARROWIA

This application is a Continuation of, and claims priority under 35 U.S.C. §120 to, International Application No. PCT/JP2010/051463, filed Jan. 27, 2010, and claims priority therethrough under 35 U.S.C. §119 to Russian Patent Application No. 2009103058, filed Jan. 30, 2009, the entireties of which are incorporated by reference herein. Also, the Sequence Listing filed electronically herewith is hereby incorporated by reference (File name: 2011-07-20T_US-421_Seq_List; File size: 33 KB; Date recorded: Jul. 20, 2011).

BACKGROUND OF THE INVENTION

1. Field of Invention

The present invention relates to the microbiological industry, and specifically to a method for producing succinic acid using yeast belonging to the genus *Yarrowia* in which the activity of succinate dehydrogenase is reduced.

2. Description of the Related Art

*Yarrowia lipolytica* is a unique yeast due to its ability to produce a wide spectrum of organic acids, including tricarboxylic acid cycle intermediates, such as citric and isocitric acids, and to secrete them into the medium. During continuous cultivation of *Y. lipolytica* N 1, oxygen requirements for growth and citric acid synthesis were found to depend on the iron concentration in the medium. A coupled effect of oxygen and iron concentrations on the functioning of the mitochondrial electron transport chain in *Y. lipolytica* N 1 was established. Based on the results obtained in continuous culture, conditions for citric acid production in a batch culture of *Y. lipolytica* N 1 have been proposed (Kamzolova S. V. et al, FEMS Yeast Res.; 3 (2):217-22 (2003)).

Succinic acid, a member of the $C_4$-dicarboxylic acid family, is widely used in the production of foods, pharmaceuticals, and biodegradable plastics. Traditionally, it is produced via chemical synthesis from petrochemical feedstocks that are nonrenewable, and these chemical processes cause environment pollution. Therefore, great attention has been paid to the use of effective natural succinic acid producers, such as microorganisms.

Most reported efforts to enhance production of the industrially valuable specialty chemical succinate have been done under anaerobic conditions, where *Escherichia coli* undergoes mixed-acid fermentation. An aerobic succinate production system was strategically designed that allows *E. coli* to produce and accumulate succinate efficiently, and the system provides the first platform for enhancing succinate production aerobically in *E. coli* based on the creation of a new aerobic central metabolic network (Lin H. et al., Biotechnol Bioeng; 89(2):148-56 (2005)).

Various *E. coli* mutant strains designed for succinate production under aerobic conditions were characterized in chemostat. The metabolite profiles, enzyme activities, and gene expression profiles were studied to better understand the metabolic network operating in these mutant strains. The most efficient succinate-producing mutant strain HL27659k has the five following mutations: sdhAB, (ackA-pta), poxB, iclR, and ptsG. It was shown that the succinate synthesis pathways engineered in strain HL27659k were highly efficient, yielding succinate as the only major product produced under aerobic conditions (Lin H. et al., Metab Eng.; 7 (5-6): 337-52 (2005)).

Fed-batch reactor experiments were performed for the strain HL27659k(pKK313) under aerobic conditions to determine and demonstrate its capacity for high-level succinate production. Results showed that the aerobic succinate production system using the designed strain HL27659k (pKK313) is more practical than conventional anaerobic succinate production systems. It has a remarkable potential for industrial-scale succinate production and process optimization (Lin H. et al., Biotechnol Bioeng; 90(6):775-9 (2005)).

A two-stage culture of NZN111, pflB ldhA double mutant, which loses its ability to ferment glucose anaerobically due to a redox imbalance, was carried out for succinic acid production. It was found that when NZN111 was aerobically cultured on acetate, it regained the ability to ferment glucose with succinic acid as the major product in subsequent anaerobic culture. Analyses of key enzyme activities revealed that the activities of isocitrate lyase, malate dehydrogenase, malic enzyme, and phosphoenolpyruvate (PEP) carboxykinase were greatly enhanced while the activities of pyruvate kinase and PEP carboxylase were reduced in the acetate-grown cells. These results indicate the great potential to take advantage of cellular regulation mechanisms for improvement of succinic acid production by a metabolically engineered *E. coli* strain (Wu H. et al., Appl Environ Microbiol.; 73(24):7837-43 (2007)).

Based on the complete genome sequence of a capnophilic succinic acid-producing rumen bacterium, *Mannheimia succiniciproducens*, gene knockout studies were carried out to understand its anaerobic fermentative metabolism and consequently to develop a metabolically engineered strain capable of producing succinic acid without by-product formation. Among three different $CO_2$-fixing metabolic reactions catalyzed by phosphoenolpyruvate (PEP) carboxykinase, PEP carboxylase, and malic enzyme, PEP carboxykinase was the most important for the anaerobic growth of *M. succiniciproducens* and succinic acid production. Oxaloacetate formed by carboxylation of PEP was found to be converted to succinic acid by three sequential reactions catalyzed by malate dehydrogenase, fumarase, and fumarate reductase. Major metabolic pathways leading to by-product formation were successfully removed by disrupting the ldhA, pflB, pta, and ackA genes. The metabolically engineered LPK7 strain was able to produce succinic acid from glucose with little or no formation of acetic, formic, and lactic acids (Lee S. J. et al., Appl Environ Microbiol.; 72(3): 1939-48 (2006)).

Growth and succinate versus lactate production from glucose by *Anaerobiospirillum succiniciproducens* was regulated by the level of available carbon dioxide and the culture pH. The succinate yield and the yield of ATP per mole of glucose were significantly enhanced when grown with excess-$CO_2$—$HCO_3^-$, which suggests that there is a threshold level of $CO_2$ for enhanced succinate production in *A. succiniciproducens*. It was shown that *A. succiniciproducens*, unlike other succinate-producing anaerobes which also form propionate, can grow rapidly and form high final yields of succinate at pH 6.2 and with excess $CO_2$—$HCO_3^-$ as a consequence of regulating electron sink metabolism (Samuelov N. S. et al., Appl Environ Microbiol.; 57 (10):3013-9 (1991)).

Chemically defined media allow for a variety of metabolic studies that are not possible with undefined media. A defined medium, AM3, was created to expand the experimental opportunities for investigating the fermentative metabolism of succinate-producing *Actinobacillus succinogenes*. *A. succinogenes* growth trends and end product distributions in AM3 and rich medium fermentations were compared. The inability to synthesize alpha-ketoglutarate from glucose indicates that at least two tricarboxylic acid cycle-associated enzyme activities are absent in *A. succinogenes* (McKinlay J. B. et al., Appl Environ Microbiol.; 71 (11): 6651-6 (2005)).

A method for producing high amounts of succinic acid under anaerobic conditions using *E. coli* strains, wherein the adhE, ldhA, iclR, arcA, and/or ack-pta genes are disrupted has been disclosed (US 20060046288 A1).

A method of producing succinic acid from industrial-grade hydrolysates by supplying an organism (*E. coli, Klebsiela, Erwinia, Lactobacillus*) that contains mutations in the genes ptsG, pflB, and ldhA, and allowing the organism to accumulate biomass and metabolize the hydrolysate has been disclosed (US 20030017559 A1).

A fermentation process for producing succinic acid by selecting a bacterial strain that does not produce high yields of succinic acid, disrupting the normal regulation of sugar metabolism of the bacterial strain, and combining the mutant bacterial strain and selected sugar in anaerobic conditions to facilitate production of succinic acid has been described. Also described is a method for changing low-yield succinic acid-producing bacteria to high-yield succinic acid-producing bacteria by selecting a bacterial strain having a phosphotransferase system and altering the phosphotransferase system so as to allow the bacterial strain to simultaneously metabolize different sugars (U.S. Pat. No. 6,159,738).

Succinate dehydrogenase (SDH) of *Saccharomyces cerevisiae* is composed of four subunits encoded by the SDH1, SDH2, SDH3, and SDH4 genes. It was determined that double disruption of the SDH1 and SDH2, or SDH1b (the SDH1 homologue) genes is required for complete loss of SDH activity and that the SDH1b gene compensates for the function of the SDH1 gene. The strain with disrupted sdh1 sdh1b genes showed an increase in succinate productivity only up to 1.9-fold along with a decrease in malate productivity relative to the wild-type strains under shaking conditions (Kubo Y. et al., J Biosci Bioeng; 90 (6):619-24 (2000)).

The pathway leading to accumulation of succinate was examined in liquid culture in the presence of a high concentration (15%) of glucose under aerobic and anaerobic conditions using a series of *Saccharomyces cerevisiae* strains in which various genes that encode the enzymes required in the TCA cycle were disrupted. Results indicate that succinate could be synthesized through two pathways, namely, alpha-ketoglutarate oxidation via the TCA cycle and fumarate reduction under anaerobic conditions (Arikawa Y. et al., J Biosci Bioeng; 87 (1):28-36 (1999)).

Methods for preparing succinic acid using a microorganism transformed with a recombinant vector containing the gene encoding a malic enzyme B (maeB), fumarate hydratase C (fumC), or formate dehydrogenases D & E (fdhD and fdhE) have been disclosed (US 20070042476 A1, US 20070042477 A1, and US 20080020436 A1, respectively).

The set of metabolic modifications responsible for coupling succinate production to the growth of the microorganism include disruption of one or more of the following genes (a) adhE, ldhA; (b) adhE, ldhA, acka-pta; (c) pfl, ldhA; (d) pfl, ldhA, adhE; (e) acka-pta, pykF, atpF, sdhA; (f) acka-pta, pykF, ptsG, or (g) acka-pta, pykF, ptsG, adhE, ldhA. (US 20070111294).

But currently, there have been no reports of reducing the activity of succinate dehydrogenase in a yeast belonging to the genus *Yarrowia* for the purpose of producing succinic acid.

SUMMARY OF THE INVENTION

Aspects of the present invention include enhancing the productivity of succinic acid in a yeast belonging to the genus *Yarrowia*, and providing a method for producing succinic acid.

The above aspects were achieved by finding that reducing the activity of succinate dehydrogenase can remarkably enhance production of succinic acid.

It is an aspect of the present invention to provide a yeast belonging to the genus *Yarrowia*, wherein said yeast produces succinic acid and activity of succinate dehydrogenase is reduced in said yeast.

It is a further aspect of the present invention to provide the yeast as described above, wherein said yeast has been modified to attenuate expression of a gene selected from the group consisting of SDH1 (YALI0D11374g), SDH2 (YALI0D23397g), SDH3 (YALI0E29667g), SDH4 (YALI0A14784g), and combinations thereof.

It is a further aspect of the present invention to provide the yeast as described above, wherein said expression of SDH1 (YALI0D11374g) is attenuated by introducing a temperature-sensitive mutation into SDH1 (YALI0D11374g).

It is a further aspect of the present invention to provide the yeast as described above, wherein said expression of SDH2 (YALI0D23397g) is attenuated by inactivating SDH2 (YALI0D23397g).

It is a further aspect of the present invention to provide the yeast as described above, wherein said yeast is *Yarrowia lipolytica*.

It is a further aspect of the present invention to provide the yeast as described above, wherein said yeast is *Yarrowia lipolytica* VKPM Y-3314.

It is a further aspect of the present invention to provide a method for producing succinic acid, which comprises cultivating the yeast as described above in a culture medium and collecting succinic acid from the culture medium.

It is a further aspect of the present invention to provide the method as described above, wherein at least a part of said cultivating is performed at below pH4.

It is a further aspect of the present invention to provide the method as described above, wherein said culture medium comprises glycerol.

It is a further aspect of the present invention to provide a method for producing a succinic acid-containing polymer, comprising the steps of producing succinic acid by the method as described above, and polymerizing succinic acid.

DETAILED DESCRIPTION OF THE PREFERRED EMBODIMENTS

Figure 1:
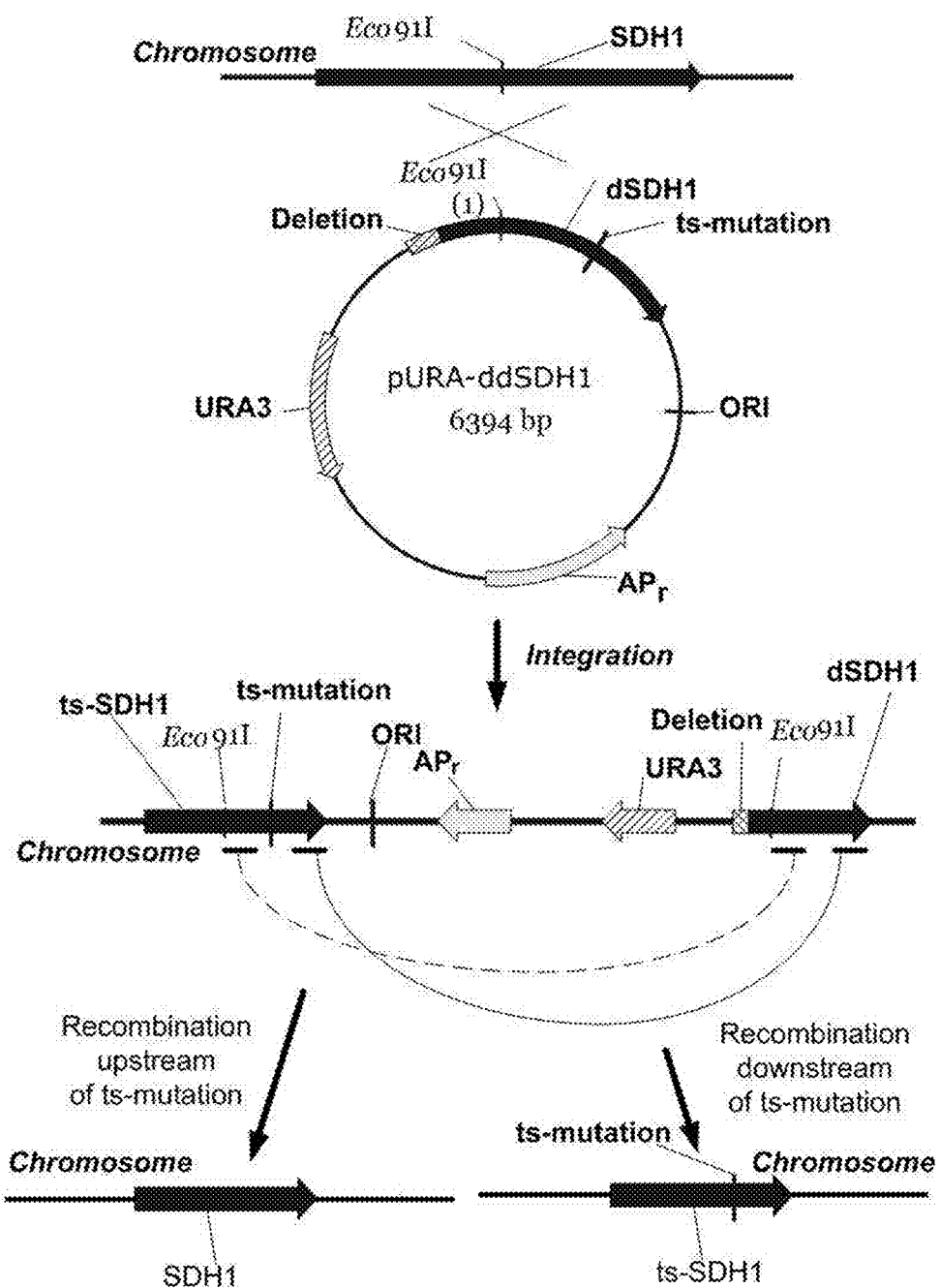
FIG. 1 shows the scheme for construction of a strain having a temperature-sensitive (ts-) mutation in SDH1 gene.

Hereinafter, the present invention will be described in detail.

The term "succinic acid" can be free succinic acid or a salt thereof depending on the pH and ions present. The terms "succinic acid" and "succinate" are used interchangeably herein.

1. Yeast

The yeast in accordance with the presently disclosed subject matter belongs to the genus *Yarrowia*, wherein said yeast produces succinic acid and in which the activity of succinate dehydrogenase is reduced.

The phrase "a yeast belonging to the genus *Yarrowia*" means that the yeast is classified into the genus *Yarrowia* according to the classification known to a person skilled in the art of microbiology. Examples of a yeast belonging to the genus *Yarrowia* include *Yarrowia lipolytica* (*Y. lipolytica*). The phrase "said yeast produces succinic acid" can mean that the yeast has the ability to produce and excrete succinic acid into a medium, when it is cultured in the medium.

The phrase "said yeast produces succinic acid" can also mean that the yeast has the ability to produce and accumulate succinic acid in an amount larger than a wild-type, non-modified, or parental strain, and can also mean that the yeast is able to cause accumulation in a medium of an amount not less than 1.0 g/L, not less than 5.0 g/L, or not less than 10.0 g/L, of succinic acid.

The phrase "(said yeast) comprises reduced activity of succinate dehydrogenase" can mean that the yeast is modified so that the succinate dehydrogenase activity in the cell is reduced as compared with an unmodified, wild type, or parental strain.

Succinate dehydrogenase (SDH) is a component of complex II of the respiratory chain that catalyses the oxidation of succinate to fumarate in the Krebs cycle and feeds electrons to the ubiquinone pool. The complex, which has been highly conserved throughout evolution, is located in the inner mitochondrial membrane and includes two catalytic and two structural subunits, all encoded by nuclear genes. In *Saccharomyces cerevisiae*, the four genes (SDH1 to SDH4) coding for SDH have been isolated and characterized. The flavoprotein subunit responsible for the oxidation of succinate to fumarate is encoded by two paralogous genes, SDH1 and SDH1b, although only SDH1 is necessary for growth on respiratory carbon sources. SDH2 codes for the iron-protein subunit that contains three different iron-sulfur centers and, together with the protein Sdh1p, constitutes the catalytic core of the SDH complex, which conveys electrons from the covalently attached flavin adenine dinucleotide (FAD) of Sdh1p first to the iron-sulfur centers and then to ubiquinone. SDH3 and SDH4 code for two small hydrophobic peptides, which anchor the complex to the inner mitochondrial membrane (Saliola M. et al., Eukaryot Cell; 3 (3): 589-97 (2004)).

The genome sequence of *Y. lipolytica* CLIB122 has been analyzed (www.ncbi.nlm.nih.gov/sites/entrez) and ORFs YALI0D11374g, YALI0D23397g, YALI0E29667g and YALI0A14784g were found to be homologous to the *S. cerevisiae* SDH1, SDH2, SDH3 and SDH4 genes, respectively. These ORFs were named SDH1, SDH2, SDH3 and SDH4, respectively. The nucleotide sequence of the SDH1 gene and the amino acid sequence of SDH1 encoded by the SDH1 gene are shown in SEQ ID NO: 1 and SEQ ID NO: 2, respectively. The nucleotide sequence of the SDH2 gene and the amino acid sequence of SDH2 encoded by the SDH2 gene are shown in SEQ ID NO: 3 and SEQ ID NO: 4, respectively. The nucleotide sequence of the SDH3 gene and the amino acid sequence of SDH3 encoded by the SDH3 gene are shown in SEQ ID NO: 5 and SEQ ID NO: 6, respectively. The nucleotide sequence of the SDH4 gene and the amino acid sequence of SDH4 encoded by the SDH4 gene are shown in SEQ ID NO: 7 and SEQ ID NO: 8, respectively.

Since there may be some differences in DNA sequences between the different strains of the genus *Yarrowia*, the SDH1, SDH2, SDH3 and SDH4 genes to be modified are not limited to the genes shown in SEQ ID No: 1, SEQ ID No: 3, SEQ ID No: 5 and SEQ ID No: 7 but can include genes homologous to SEQ ID No: 1, SEQ ID No: 3, SEQ ID No: 5 and SEQ ID No: 7 which encode a variant protein of the SDH1, SDH2, SDH3, and SDH4 proteins, respectively. The term "variant protein" means a protein which has changes in the sequence, whether they are deletions, insertions, additions, or substitutions of amino acids, but still maintains the activity of the product as the SDH1/SDH2/SDH3/SDH4 protein(s). The number of changes in the variant protein depends on the position in the three dimensional structure of the protein or the type of amino acid residues. It can be 1 to 30, in another example 1 to 15, and in another example 1 to 5 in SEQ ID No: 2, SEQ ID No: 4, SEQ ID No: 6 and SEQ ID No: 8. These changes in the variants can occur in regions of the protein that are not critical for the function of the protein. This is because some amino acids have high homology to one another so the three dimensional structure or activity is not affected by such a change. Therefore, the protein variant encoded by the SDH1, SDH2, SDH3 and SDH4 genes can be one which has a homology of not less than, for example, 80%, in another example not less than 90%, in another example not less than 95%, and in another example not less than 98%, with respect to the entire amino acid sequence shown in SEQ ID No: 2, SEQ ID No: 4, SEQ ID No: 6 and SEQ ID No: 8, as long as the activity of the SDH1, SDH2, SDH3, or SDH4 protein(s) prior to modification is maintained.

Homology between two amino acid sequences can be determined using well-known methods, for example, the computer program BLAST 2.0, which calculates three parameters: score, identity and similarity.

The substitution, deletion, insertion or addition of one or several amino acid residues can be conservative mutation(s) so that the activity is maintained. The representative conservative mutation can be a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Moreover, the SDH1, SDH2, SDH3, and SDH4 genes can be variants which hybridize under stringent conditions with the nucleotide sequence complementary to the sequence shown in SEQ ID No: 1, SEQ ID No: 3, SEQ ID No: 5, and SEQ ID No: 7, respectively, or a probe which can be prepared from the nucleotide sequence under stringent conditions, provided that it encodes a functional protein prior to inactivation. "Stringent conditions" include those under which a specific hybrid, for example, a hybrid having homology of not less than 70%, in another example not less than 80%, in another example not less than 90%, in another example not less than 95%, and in another example not less than 98%, is formed and a non-specific hybrid, for example, a hybrid having homology lower than the above, is not formed. For example, stringent conditions are exemplified by washing one time or more, in another example two or three times at a salt concentration of 1×SSC, 0.1% SDS, in another example 0.1×SSC, 0.1% SDS at 60° C. Duration of washing depends on the type of membrane used for blotting and, as a rule, can be what is recommended by the manufacturer. For example, the recommended duration of washing for the Hybond™ N+ nylon membrane (Amersham) under stringent conditions is 15 minutes. Washing can be performed 2 to 3 times. The length of the probe can be suitably selected depending on the hybridization conditions, and is usually 100 by to 1 kbp.

The succinate dehydrogenase activity in the yeast can be reduced by attenuating expression of one or more of the SDH1, SDH2, SDH3 and SDH4 genes. In order to attenuate expression of the gene, the yeast can be modified so that the cell contains a reduced amount of the protein encoded by the gene as compared with an unmodified yeast, or the cell is unable to synthesize the protein encoded by the gene. Such modification of the yeast can be done by altering an expression regulating sequence of the gene such as the promoter, Shine-Dalgarno (AD) sequence, etc. In addition, expression of the SDH1, SDH2, SDH3, or SDH4 gene can be attenuated by introducing a mutation into the gene on the chromosome so that intracellular activity of the protein encoded by the gene is decreased as compared with that of an unmodified strain. Such a mutation on the gene can be the introduction of insertion of a drug-resistance gene, or the deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). The activity of the protein encoded by the gene can also be reduced by replacement of one base or more in the gene to cause an amino acid substitution in the protein (missense mutation), introduction of a stop codon (nonsense mutation), deletion of one or two bases to cause a frame shift.

For example, the following methods can be employed to introduce a mutation by gene recombination. A mutant gene encoding a mutant protein having a decreased activity is prepared, and the yeast to be modified can be transformed with a DNA fragment containing the mutant gene, and after the native gene on the chromosome is replaced with the mutant gene by homologous recombination, the resulting strain (having the native gene on the chromosome replaced with the mutant gene) can be selected. Such site-specific mutation by gene replacement using homologous recombination has already been established. In the Examples described below, a temperature-sensitive mutation was introduced into the SDH1 gene on the chromosome of *Y. lipolytica* Po1f (ATCC MYA-2613). Due to the mutation, the expression of the SDH1 gene is attenuated and the succinate dehydrogenase activity is reduced at a higher temperature (32° C.) in the obtained strains, Po1f (SDH1-ts-0134) and Po1f (SDH1-ts-2007).

Expression of the SDH1, SDH2, SDH3, or SDH4 gene can also be attenuated by inactivating the gene. The phrase "inactivating gene" can mean that the modified gene encodes a completely inactive protein. It is also possible that the modified DNA region is unable to naturally express the gene due to the deletion of a part of or the entire gene, the shifting of the reading frame of the gene, the introduction of missense/nonsense mutation(s), or the modification of an adjacent region of the gene, including sequences controlling gene expression, such as promoter(s), enhancer(s), attenuator(s), ribosome-binding site(s), etc.

The above-mentioned gene substitution can be carried out as follows. That is, yeast is transformed with a recombinant DNA containing a mutant gene to cause recombination between the mutant gene and the corresponding chromosomal gene. Then, the marker gene that is inserted into the recombinant DNA based on a characteristic such as auxotrophy of the host makes the manipulation easy. Furthermore, making the above-mentioned recombinant DNA linear, for example, by cleavage with a restriction enzyme and, in addition, removal of a replication control region that functions in yeasts from the recombinant DNA, can efficiently give rise to a strain in which the recombinant DNA is integrated into the chromosome. In the Examples to be described below, the SDH2 gene on the chromosome of *Y. lipolytica* Po1f (ATCC MYA-2613) was inactivated to obtain Po1f(dSDH2), which produces succinic acid and includes reduced activity of succinate dehydrogenase. From among mutants of Po1f (dSDH2), *Y. lipolytica* VKPM Y-3314 was selected for its ability to produce a greater amount of succinic acid.

Expression of the gene can be attenuated or the gene can be inactivated also by insertion of a transposon or an IS factor into the coding region of the gene (U.S. Pat. No. 5,175,107), or by conventional methods, such as a mutagenesis treatment using UV irradiation and nitrosoguanidine (N-methyl-N'-nitro-N-nitrosoguanidine), or methoxylamine.

Methods for the preparation of plasmid DNA, digestion and ligation of DNA, transformation, selection of an oligonucleotide as a primer, and the like can be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989). For the transformation of yeasts, those methods conventionally used in the transformation of yeasts, such as a protoplast method, an electroporation method, or the like can be employed.

2. Methods

The methods are described for producing succinic acid which include cultivating the yeast as described herein in a culture medium to produce and excrete succinic acid into the medium, and collecting succinic acid from the medium.

The cultivation, collection, and purification of succinic acid from the medium and the like can be performed in a manner similar to conventional fermentation methods wherein succinic acid is produced using a microorganism.

The medium used for culture can be either a synthetic or natural medium, so long as the medium includes a carbon source, a nitrogen source, minerals and, if necessary, appropriate amounts of nutrients which the yeast requires for growth. The carbon source can include various carbohydrates such as glucose and sucrose, and various organic acids. Depending on the mode of assimilation of the used microorganism, alcohol, including ethanol and glycerol, can be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as a shaking culture, and a stirring culture with aeration, at a temperature of 20 to 40° C., and in another example 24 to 32° C. The pH of the culture is usually between 2 and 9, in another example between 3 and 7.5. The pH of the culture can be adjusted with ammonia, calcium carbonate, various bases, and buffers. Alternatively, the cultivation can be performed without pH control and, after pH of the medium is decreased, maintained under an acidic condition where the major accumulation of succinic acid occurs. At least a part of the cultivation can be maintained at below pH4 so that more succinic acid is produced. Usually, a 1 to 7-day cultivation leads to the accumulation of succinic acid in the liquid medium.

After cultivation, solids such as cells can be removed from the liquid medium by centrifugation or membrane filtration, and then succinic acid can be collected and purified by ion-exchange, concentration, and/or crystallization methods.

Furthermore, after the production of succinic acid, a polymerization reaction may be carried out using the obtained succinic acid as a raw material to produce a succinic acid-containing polymer. In recent years, while the number of environment-friendly industrial products is on the increase, polymers prepared by using raw materials of a plant origin have been attracting attention. The produced succinic acid produced can then be processed into polymers such as polyester and polyamide. Specific examples of the succinic acid-containing polymer include a succinic acid polyester obtained through polymerization between a diol such as butanediol or ethylene glycol and succinic acid, and a succinic acid polyamide obtained through polymerization between a diamine such as hexamethylenediamine and succinic acid. In addition, the succinic acid or a composition containing the succinic acid can be used for food additives, pharmaceuticals, cosmetics, and the like.

EXAMPLES

The present invention will be more concretely explained below with reference to the following non-limiting Examples.

Example 1

Construction of a Strain Having a Temperature-Sensitive (ts-) Mutation in the SDH1 Gene 1. Construction of the Plasmid pURA-ddSDH1

First, a DNA fragment containing the URA3 gene was obtained using PCR. Primers P1 (SEQ ID NO: 9) and P2 (SEQ ID NO: 10) were used in the PCR. The entire genomic DNA of *Y. lipolytica* W29 (CLIB (Collection de Levures d'Interet Biotechnologique, 78850 Thiverval Grignon, France (Collection of Yeasts of Biotechnological Interest)) accession number CLIB89) was isolated using the method described by Kaiser et al. (1994 Methods in Yeast Genetics. Cold Spring Harbor, N.Y.: Cold Spring Harbor Laboratory), and was used as the template in the PCR reaction. The *Y. lipolytica* W29strain can also be obtained from the ATCC (ATCC20460).

A 1972 by PCR product was obtained and purified in a 1% agarose gel. The PCR product (0.5 μg) was ligated with pUC19 (0.2 μg), which had been previously treated with Ecl136II endonuclease. The obtained plasmid was used for electroporation of the *E. coli* strain XL-1 (Blue) (Stratagene, catalog #200228) as described by Sambrook et al. (Molecular Cloning, second edition, Cold Spring Harbor Laboratory, Plainview, N.Y. (1989)). Clones containing target insertion were selected by plating onto an L-agar plate containing 100 μg/ml of ampicillin and by testing for absence of β-galactosidase activity. Plasmid DNA was isolated from selected clones and was tested using restriction analysis. The obtained plasmid (4658 bp) contained the URA3 gene of *Y. lipolytica* and its regulatory regions. The plasmid was named pUC-URA3.

To obtain a DNA fragment containing the SDH1 gene having a deletion, two DNA fragments were obtained using PCR. The PCR reaction was performed using the entire genomic DNA of *Y. lipolytica* W29 as the template and primers P3 (SEQ ID NO: 11) and P4 (SEQ ID NO: 12), and P5 (SEQ ID NO: 13) and P6 (SEQ ID NO: 14), and DNA fragments of 1223 by and 1768 bp, respectively, were obtained. Pfu polymerase was used in PCR. The obtained PCR products were purified in a 1% agarose gel and then the DNA fragments (0.05 μg each) were used as the template in PCR using Pfu polymerase and primers P3 and P6. A 2968 by PCR product was obtained and purified in a 1% agarose gel. The PCR product (0.5 μg) was treated with endonucleases XbaI and HindIII and then ligated with the plasmid pUC-URA3, which had been previously treated with endonucleases XbaI and HindIII followed by dephosphorylating using alkaline phosphatase CIAP. The obtained plasmid was used for electroporation of the *E. coli* strain XL-1 (Blue). Clones of transformants were selected by plating onto an L-agar plate containing 100 μg/ml of ampicillin. Plasmid DNA was isolated from the selected clones. The obtained plasmid (7608 bp) contained the *Y. lipolytica* SDH1 gene having a deletion of 195 by and the regulatory regions. The plasmid was named pUC-URA3-dSDH1.

The plasmid pUC-URA3-dSDH1 (0.05 μg) was treated with endonucleases XbaI and XmaJI. The larger of the obtained DNA fragments was purified in a 1% agarose gel. The 6394 by DNA fragment obtained after treating with ligase T4 was used for electroporation of the *E. coli* strain XL-1 (Blue). Clones of transformants were selected by plating onto an L-agar plate containing 100 μg/ml of ampicillin. Plasmid DNA was isolated from the selected clones and was tested using restriction analysis. The obtained plasmid (6394 bp) contained most of the ORF of *Y. lipolytica* SDH1 gene and the terminator. The plasmid was named pURA-ddSDH1.

2. Construction of the Strains Po1f/pURA-ddSDH-ts No. 2007 and Po1f/pURA-ddSDH-ts No. 0134.

The plasmid pURA-ddSDH1 (15 μg) was treated in vitro with methoxylamine as described in Kadonaga J. T and Knowles J. R., N.A.R., 13 (5), 1733-45 (1985). DNA from the solution after dialysis was precipitated using ethanol, washed, and used for electroporation of the *E. coli* strain XL-1 (Blue). Clones of transformants were selected by plating onto an L-agar plate containing 100 μg/ml of ampicillin.

107 transformants were grown overnight in 200 ml LB supplemented with ampicillin (100 μg/ml). Grown cultures were used for isolation of DNA. The obtained mutagenized plasmid pURA-ddSDH1 library was treated with endonuclease Eco91I and used for transformation of *Y. lipolytica* Po1f (ATCC MYA-2613) as described in Current Genetic, 1989, vol 16, pp. 253-260. The Po1f strain can be obtained from American Type Culture Collection. (P.O. Box 1549 Manassas, Va. 20108, United States of America). Clones of transformants were selected by plating onto minimal medium YNB-agar supplemented with glucose (2%), leucine (0.01%) and casamino acids (0.2%). 3000 transformants were grown for 3 days in liquid minimal medium YNB supplemented with glucose (0.1%), leucine (0.01%) and sodium succinate (2%) at 20° C., pH 6.8 with aeration at 1200 rpm. Clones that grew were plated (each clone onto two plates) onto YNB-agar supplemented with leucine (0.01%) and sodium succinate (1%), pH 6.8. Two series of plates were cultivated in parallel for 3 days at 20° C. and 32° C. Clones that grew significantly better at 20° C. as compared to 32° C. were tested by a similar manner to confirm its sensitivity to temperature. As can be seen in FIG. 1, after integration of the plasmid pURA-ddSDH into the chromosome, only the remaining copy of the SDH1 gene can be expressed. The part of this gene copy (downstream of the Eco91I site) is inherent to the inserted plasmid and therefore can contain mutations. Thus, the obtained transformants correspond to a mutant SDH1 gene library.

To verify integration of the plasmid pURA-ddSDH into the proper locus on the chromosome, PCR was performed using Taq-polymerase. Locus-specific primers P7 (SEQ ID NO: 15) and P8 (SEQ ID NO: 16) and the entire genomic DNA isolated from selected transformants were used in PCR for the verification. Thus, two transformants were selected for further study: Po1f/pURA-ddSDH-ts No. 0134 and Po1f/pURA-ddSDH-ts No. 2007 harboring mutations Ser675Phe and Glu483Lys, respectively, in the SDH1 gene. The strains were named Po1f(SDH1-ts-0134) and Po1f(SDH1-ts-2007), respectively.

Example 2

Construction of a Strain with an Inactivated SDH2 Gene

First, three DNA fragments containing the promoter region of the SDH2 gene (1125 bp), the URA3 gene (1229 bp), and the terminator region of the SDH2 gene (1018 bp), were obtained by PCR using Pfu polymerase, the entire genomic DNA of *Y. lipolytica* W29 (ATCC 20460) and primer sets P9 (SEQ ID NO: 17) and P10 (SEQ ID NO: 18), P11 (SEQ ID NO: 19) and P12 (SEQ ID NO: 20), and P13 (SEQ ID NO: 21) and P14 (SEQ ID NO: 22), respectively. The PCR products were purified in a 1% agarose gel. PCR products containing the promoter region of the SDH2 gene (1125 bp) and the URA3 gene (1229 bp) were used as the template in PCR using Pfu polymerase and primers P9 and P12. The PCR product (2333 bp) was purified in a 1% agarose gel. Then, the purified PCR product (2333 bp) and the PCR product containing the terminator region of the SDH2 gene (1018 bp) were used as the template in PCR using Pfu polymerase and primers P9 and P14. The PCR product (3330 bp) was purified in a 1% agarose gel and then 1 μg of the PCR product was used for transformation of *Y. lipolytica* Po1f by a method using lithium acetate. Clones of transformants were selected by plating onto minimal medium YNB-agar supplemented with glycerol (5% v/v), leucine (0.01%), and casamino acids (0.2%). Selected transformants were then tested for the ability to grow in culture medium containing succinate as the sole source of carbon. Insertion into SDH2 locus was verified using PCR. Taq-polymerase, the entire genomic DNA isolated from selected transformants as the template and locus-specific primers P15 (SEQ ID NO: 23) and P16 (SEQ ID NO: 24) were used in PCR for the verification. One transformant, named Po1f(dSDH2), was selected for further study.

Example 3

Production of Succinic Acid by *Y. lipolytica* Strains Po1f(SDH1-ts-0134), Po1f(SDH1-ts-2007) and Po1f(dSDH2)

To test the effect of attenuating the expression of the genes SDH1 (YALI0D11374g) or SDH2 (YALI0D23397g) on succinate production, the productivity of the strains Po1f(SDH1-ts-0134), Po1f(SDH1-ts-2007), Po1f(dSDH2) and Po1f were compared.

The strains Po1f(SDH1-ts-0134), Po1f(SDH1-ts-2007), and Po1f (the initial titre of cells was $1-5*10^5$ cell/ml) were each cultivated in 5 ml minimal medium YNB (Himedia) supplemented with glycerol (5% (v/v)), uracyl, and leucine (0.01%), pH=6.8 (adjusted with 50 mM phosphate buffer) in 50 ml test tubes at 24° C. After 2 days of incubation 2.5% $CaCO_3$ was added into the medium to adjust the pH. When the titer of cells reached $(0.8-1)*10^7$, some test tubes were transferred so they were cultivated at 32° C., and others were cultivated at 24° C. After 5 days of cultivation, the amount of succinic acid, α-ketoglutaric acid, citric acid, pyruvic acid, and acetic acid which had accumulated in the medium, and the concentration of glycerol in the culture broth, were determined by HPLC. The results of two independent test tube fermentations are shown in Table 1. As follows from Table 1, Po1f(SDH1-ts-0134) and Po1f(SDH1-ts-2007) produced a higher amount of succinic acid when the cultivation temperature was 32° C. Po1f produced only a small amount of succinic acid at this temperature.

The strains Po1f(dSDH2) and Po1f ($10^5$ cell/ml) were each cultivated in 10 ml minimal medium YNB (Himedia) supplemented with glycerol (5% (v/v)), leucine (0.01%), uracyl (0.01%) (for Po1f only), pH=6.8 (adjusted with 50 mM phosphate buffer) in 50 ml test tubes at 30° C. After 3 days of incubation, 2.5% $CaCO_3$ was added into the medium to adjust the pH. After 7 days of cultivation, the amount of succinic acid, α-ketoglutaric acid, citric acid, pyruvic acid, and acetic acid which had accumulated in the medium, and the concentration of glycerol in the culture broth, were determined by HPLC. The results of the test tube fermentations are shown in Table 1. As follows from Table 1, Po1f (dSDH2) produced a higher amount of succinic acid, as compared with Po1f.

The strains Po1f(dSDH2) and Po1f were each cultivated in 50 ml medium YPG (1% yeast extract, 2% peptone, 5% (v/v) glycerol), in 750 ml flasks at 30° C. After 2 days of incubation 2.5% $CaCO_3$ was added into medium. After 5 days of cultivation, the amount of succinic acid, α-ketoglutaric acid, citric acid, pyruvic acid, and acetic acid which had accumulated in the medium, and the concentration of glycerol in the culture broth, were determined by HPLC. The results of flask fermentations are shown in Table 2. As follows from Table 2, Po1f(dSDH2) produced a larger amount of succinic acid, as compared with Po1f.

TABLE 1

| Strain | T °C. | Organic acid | | | | | Glycerol g/l |
|---|---|---|---|---|---|---|---|
| | | SA, g/l | KG, g/l | CA, g/l | PA, g/l | AA, g/l | |
| Po1f (SDH1-ts-0134) | 32 | 11.51 | 2.61 | 3.00 | 6.28 | 6.32 | 1.55 |
| | 24 | 1.05 | 0.64 | 7.07 | 1.95 | 0.96 | 0.81 |
| Po1f (SDH1-ts-2007) | 32 | 17.01 | 1.60 | 2.11 | 3.31 | 9.94 | 0.37 |
| | 24 | — | 1.06 | 8.87 | 2.14 | 0.83 | 0.40 |
| Po1f | 32 | 1.24 | 1.14 | 3.24 | 1.99 | 0.78 | — |
| | 24 | — | 0.23 | 1.33 | — | 0.85 | 0.19 |
| Po1f (dSDH2) | 30 | 16.58 | 2.25 | 0.57 | 2.5 | 12.65 | — |
| Po1f | 30 | 0.6 | 4.15 | 0.8 | 1.5 | — | — |

SA—Succinic acid,
KG—α-ketoglutaric acid,
CA—citric acid,
PA—pyruvic acid,
AA—acetic acid

TABLE 2

| Strain | Exp. No. | Organic acid | | | | | cells/ ml | Glycerol g/l |
|---|---|---|---|---|---|---|---|---|
| | | SA, g/l | KG, g/l | CA, g/l | PA, g/l | AA, g/l | | |
| Po1f (dSDH2) | 1 | 24.0 | 0.5 | 6.14 | 2.94 | 12.2 | $1.1*10^9$ | 1.94 |
| Po1f | 1 | — | 1.4 | 6.37 | — | 1.02 | $1.2*10^9$ | — |

SA—Succinic acid,
KG—α-ketoglutaric acid,
CA—citric acid,
PA—pyruvic acid,
AA—acetic acid

Example 4

Selection of *Y. lipolytica* Strain VKPM Y-3314

To improve the growth of the strain Po1f(dSDH2), mutagenesis was performed as follows. The cells of the strain Po1f (dSDH2) were grown in YPG medium (see Example 3) until the titer of cells reached $10^9$ cells/ml, then cells were harvested using centrifugation, triple washed with physiological solution, and resuspended in 50 mM K-phosphate buffer (pH=6.8) so that titer of cells was $1\text{-}3*10^8$ cells/ml. 1 ml of this suspension was treated with N-methyl-N'-nitro-N-nitrosoguanidine (40 μg/ml) for 2 hours at 30° C. Then, the cells were triple washed with physiological solution and plated (titer of cells was $10^8$ or $10^9$ cells/ml) onto YNB medium, containing leucine (0.1 g/l), and glycerol (2%, v/v). The survival value was 2.8%. After 5 days of growing there were some large-size colonies among the colonies having normal size (1-2 for $10^4$). 50 large-size colonies were chosen and replated onto the same medium.

All 50 chosen strains and the strains Po1f(dSDH2) and Po1f as a control were each inoculated in 5 ml of medium YPG to obtain a titer of cells $\sim 5*10^5$ cells/ml. After 7 days of cultivation at 30° C. without the use of buffers and without adding $CaCO_3$, the amounts of succinic acid, α-ketoglutaric acid, citric acid, pyruvic acid, and acetic acid were determined using HPLC. The results of test tube fermentations are shown in Table 3. As follows from Table 3, most mutants produced a larger amount of succinic acid, as compared with the strains Po1f(dSDH2) and Po1f. It was observed that the pH value of the cultivation medium reached 3.2-3.5 after 3-4 days of fermentation. The best succinic acid-producing mutant strain No. 18 was chosen for further study. This strain was deposited in the Russian National Collection of Industrial Microorganisms (Russia, 117545 Moscow, 1 Dorozhny proezd, 1) on Nov. 15, 2007 under accession No. VKPM Y-3314. Then, the deposit was converted to an international deposit under the provisions of the Budapest Treaty on Dec. 23, 2009.

TABLE 3

| Mutant No. | Organic acid | | | | |
|---|---|---|---|---|---|
| | SA, g/l | PA, g/l | CA, g/l | AA, g/l | KG, g/l |
| 1 | 7.3 | 5.44 | 3.95 | 4.12 | 1.05 |
| 2 | 14.65 | 5.25 | 4.1 | 4.97 | 2.82 |
| 3 | 3.3 | 0 | 2.58 | 5.79 | 0 |
| 4 | 14.59 | 4.69 | 4.06 | 3.28 | 2.44 |
| 5 | 12.37 | 5.96 | 3.5 | 4.79 | 2.37 |
| 6 | 3.18 | 0 | 1.16 | 6.21 | 0 |
| 7 | 15.52 | 6.4 | 3.96 | 4.53 | 2.39 |
| 9 | 15.97 | 4.36 | 3.37 | 4.47 | 3.03 |
| 10 | 13.34 | 5.93 | 3.62 | 4.43 | 2.43 |
| 12 | 10.5 | 6.95 | 3.56 | 4.31 | 1.51 |
| 13 | 7.6 | 6.96 | 3.92 | 5.17 | 1.48 |
| 14 | 3.46 | 0 | 2.4 | 5.63 | 0 |
| 15 | 15.73 | 4.11 | 4.24 | 4.1 | 3.04 |
| 16 | 14.89 | 4.33 | 4.54 | 4.02 | 2.91 |
| 17 | 12.18 | 7.45 | 4.36 | 4.17 | 2.02 |
| 18 | 19.88 | 4.38 | 4.34 | 4.75 | 3.98 |
| 19 | 13.54 | 5.96 | 3.67 | 5.25 | 2.09 |
| 20 | 17.32 | 4.54 | 3.78 | 4.75 | 2.61 |
| 21 | 15.68 | 4.57 | 3.88 | 4.49 | 2.48 |
| 22 | 6.35 | 5.25 | 4.02 | 4.36 | 0.62 |
| 23 | 6.4 | 0 | 3.99 | 5.39 | 1.15 |
| 24 | 18.39 | 3.71 | 3.8 | 4.27 | 2.72 |
| 28 | 19.05 | 4.26 | 4.2 | 4.71 | 2.89 |
| 29 | 14.35 | 6.39 | 3.96 | 5.46 | 1.97 |
| 30 | 19.44 | 4.59 | 4.2 | 4.89 | 3.11 |
| 31 | 16.43 | 5.72 | 4.35 | 6.05 | 2.82 |
| 32 | 7.46 | 6.36 | 3.95 | 5.69 | 1.23 |
| 34 | 17.91 | 3.56 | 3.73 | 4.23 | 2.89 |
| 35 | 12.97 | 6.23 | 3.8 | 5.5 | 2.07 |
| 36 | 13.76 | 6.93 | 3.88 | 5.01 | 2.31 |
| 37 | 6.76 | 5.47 | 4.17 | 4.74 | 0.67 |
| 41 | 16.65 | 4.42 | 3.64 | 4.66 | 2.33 |
| 43 | 13.65 | 7.52 | 4.16 | 5.28 | 1.89 |
| 44 | 6.63 | 4.12 | 3.67 | 4.23 | 1.27 |
| 45 | 7.13 | 5.48 | 4.01 | 5.15 | 1.15 |
| 47 | 10.77 | 6.49 | 3.93 | 4.78 | 1.52 |
| 48 | 10.2 | 8.81 | 4.22 | 6.28 | 1.13 |
| Po1f(dSDH2) | 3.7 | 0 | 2.5 | 7.24 | 0 |
| Po1f | 3.18 | 0 | 4.75 | 0 | 2.66 |

SA—Succinic acid,
KG—α-ketoglutaric acid,
CA—citric acid,
PA—pyruvic acid,
AA—acetic acid

Example 5

Production of Succinic Acid by *Y. lipolytica* Strain VKPM Y-3314

The *Y. lipolytica* strain VKPM Y-3314 was cultivated in 5 ml of YPG medium containing glycerol (5%, v/v) of different manufacturers in 50 ml test tubes. The initial titre of cells was $\sim 5*10^5$ cells/ml. The first series of experiments was performed with the addition of $CaCO_3$ (2.5%) on the $3^{rd}$ day of cultivation. The second series of experiments was performed without adding $CaCO_3$. The pH of the medium, and the concentrations of organic acids and residual glycerol are presented in Table 4 for the first series of experiments and Table 5 for the second series of experiments. As follows from Table 4 and Table 5, the *Y. lipolytica* strain VKPM Y-3314 produced succinic acid in the both series of experiments using glycerol of different manufactures.

Figure 2:
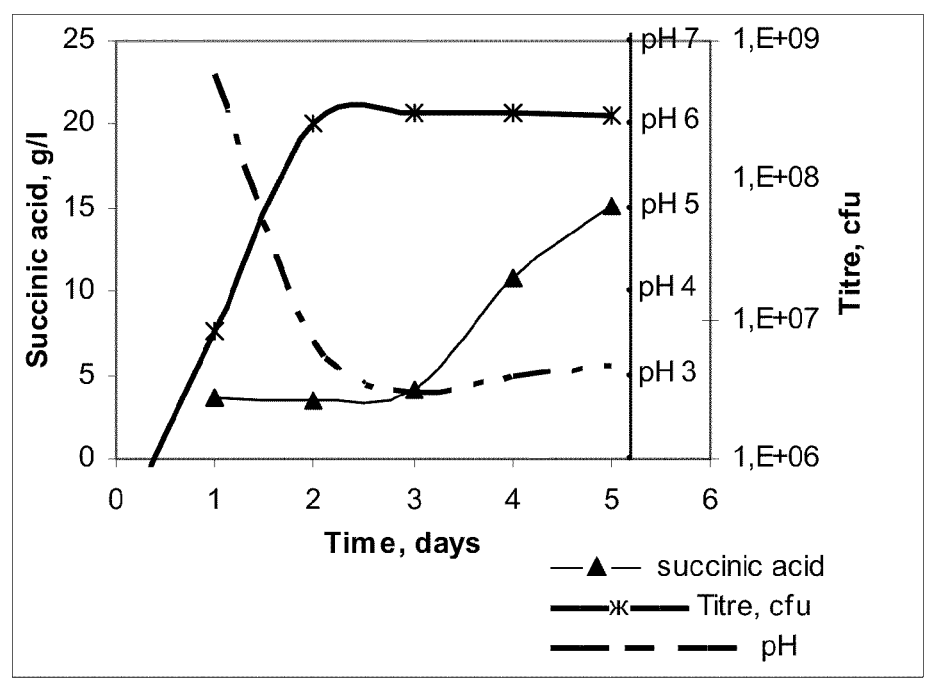
FIG. 2 shows growth curves, pH, and concentration of succinic acid during cultivation of the strain *Y. lipolytica* VKPM Y-3314.

The *Y. lipolytica* strain VKPM Y-3314 was also cultivated in a 750 ml flask in 50 ml of YPG medium containing glycerol (5%, v/v). The initial titre of cells was $\sim 2.5*10^5$ cells/ml. Every 24 h during fermentation, samples were collected, and the titre of cells, medium pH, and the concentration of succinic acid were measured in the samples. The results are presented in FIG. 2. As follows from FIG. 2, cells of the *Y. lipolytica* strain VKPM Y-3314 produced succinic acid at a low pH, below pH4.

TABLE 4

| Manufacturer of glycerol | Days of ferment. | Organic acid | | | | | Residual glycerol, g/l | pH |
|---|---|---|---|---|---|---|---|---|
| | | SA, g/l | KG, g/l | CA, g/l | PA, g/l | AA, g/l | | |
| Sigma | 5 | 23.53 | 1.21 | 1.07 | 2.66 | 4.44 | 0 | 6.12 |
| | 7 | | | | | | 0 | 5.65 |
| Nowit DCA-F | 5 | 28.22 | 2.49 | 1.12 | 2.21 | 3.06 | 0 | 6 |
| | 7 | | | | | | 0 | 5.63 |
| R glycerine | 5 | 26.92 | 1.55 | 1.08 | 1.91 | 3.38 | 0 | 6.1 |
| | 7 | | | | | | 0 | 5.62 |
| Glyrex | 5 | 25.34 | 1.55 | 1.49 | 2.02 | 3.54 | 4.87 | 6.15 |
| | 7 | | | | | | 0 | 5.74 |

SA—Succinic acid,
KG—α-ketoglutaric acid,
CA—citric acid,
PA—pyruvic acid,
AA—acetic acid

TABLE 5

| Manufacturer of glycerol | Days of ferment. | Organic acid | | | | | Residual glycerol, g/l | pH |
|---|---|---|---|---|---|---|---|---|
| | | SA, g/l | KG, g/l | CA, g/l | PA, g/l | AA, g/l | | |
| Sigma | 5 | 20.27 | 2 | 1.15 | 2.72 | 4.04 | 0 | 3.75 |
| | 7 | | | | | | 0 | 3.24 |
| Nowit DCA-F | 5 | 22.6 | 2.4 | 1.23 | 2.93 | 2.98 | 6.22 | 3.5 |
| | 7 | | | | | | | 3.13 |
| R glycerine | 5 | 26.67 | 2.35 | 1.16 | 2.11 | 3.03 | 2.16 | 3.6 |
| | 7 | | | | | | | 3.12 |
| Glyrex | 5 | 18.67 | 1.69 | 1.7 | 2.67 | 3.12 | 10.89 | 3.65 |
| | 7 | | | | | | | 3.4 |

SA—Succinic acid,
KG—α-ketoglutaric acid,
CA—citric acid,
PA—pyruvic acid,
AA—acetic acid While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

The invention claimed is:

1. A yeast belonging to the genus *Yarrowia*, wherein said yeast produces succinic acid and has been genetically modified to attenuate expression of SDH1 (YALI0D11374g) by introducing a temperature-sensitive mutation into SDH1 (YALI0D11374g).

2. The yeast according to claim 1, wherein said yeast is *Yarrowia lipolytica*.

3. The yeast according to claim 1, wherein said yeast is *Yarrowia lipolytica* VKPM Y-3314.

4. A method for producing succinic acid, which comprises cultivating the yeast according to claim 1 in a culture medium and collecting succinic acid from the culture medium.

5. The method according to claim 4, wherein at least a part of said cultivating is performed at below pH4.

6. The method according to claim 4, wherein said culture medium comprises glycerol.

7. A method for producing a succinic acid-containing polymer, comprising the steps of producing succinic acid by the method according to claim 4, and polymerizing said succinic acid.

* * * * *

SEQUENCE LISTING

<160> NUMBER OF SEQ ID NOS: 24

<210> SEQ ID NO 1
<211> LENGTH: 2136
<212> TYPE: DNA
<213> ORGANISM: Yarrowia lipolytica
<220> FEATURE:
<221> NAME/KEY: CDS
<222> LOCATION: (1)..(2136)

<400> SEQUENCE: 1

```
atg tca gac tgt ctt gaa aat ttc agt ctg tca acc gcc gat gct ctc      48
Met Ser Asp Cys Leu Glu Asn Phe Ser Leu Ser Thr Ala Asp Ala Leu
1               5                   10                  15 aca gtc tat ccc cac aac aca ccc tct gat acc aca act ata tac          96
Thr Val Tyr Pro His Asn Thr Pro Ser Asp Thr Thr Thr Ile Tyr
            20                  25                  30 agt cac tgc gga cca ctc tgc agt aaa tca tcc aga caa cta ttc tct     144
Ser His Cys Gly Pro Leu Cys Ser Lys Ser Ser Arg Gln Leu Phe Ser
        35                  40                  45
```

-continued

```
acc tac cgg aat acg caa aac acc tct cca ccc cac aac gcc tgc aga         192
Thr Tyr Arg Asn Thr Gln Asn Thr Ser Pro Pro His Asn Ala Cys Arg
 50                  55                  60 aaa ccc cac aac aca act aac aca gaa atg ctt aga gct atc aaa aac         240
Lys Pro His Asn Thr Thr Asn Thr Glu Met Leu Arg Ala Ile Lys Asn
 65                  70                  75                  80 ccc cga gcc gtt ctc aag tct cgt cac ttc tcc acc tcc ccg gtg gtg         288
Pro Arg Ala Val Leu Lys Ser Arg His Phe Ser Thr Ser Pro Val Val
                 85                  90                  95 gcc aag gtc ttc gcc aac ggc ccc gtc aag gcc cag gag gcc ccc tcc         336
Ala Lys Val Phe Ala Asn Gly Pro Val Lys Ala Gln Glu Ala Pro Ser
             100                 105                 110 cac gtg gcg tcc aag tac gcc gtc gtc gac cac gag tac gat tgt gtt         384
His Val Ala Ser Lys Tyr Ala Val Val Asp His Glu Tyr Asp Cys Val
             115                 120                 125 gtt gtt gga gcc ggt gga gcc ggt ctc cga gcc gcc ttc ggt ctg gcc         432
Val Val Gly Ala Gly Gly Ala Gly Leu Arg Ala Ala Phe Gly Leu Ala
130                 135                 140 gag gct ggc ttc aac acc gct tgt atc tcc aag ctg ttc ccc acc cga         480
Glu Ala Gly Phe Asn Thr Ala Cys Ile Ser Lys Leu Phe Pro Thr Arg
145                 150                 155                 160 tcc cac acc gtc gct gcg cag gga ggt atc aac gcc gct ctc gga aac         528
Ser His Thr Val Ala Ala Gln Gly Gly Ile Asn Ala Ala Leu Gly Asn
                165                 170                 175 atg cac ccc gat aac tgg aag tgg cac atg tat gac acc gtc aag ggt         576
Met His Pro Asp Asn Trp Lys Trp His Met Tyr Asp Thr Val Lys Gly
            180                 185                 190 tcc gat tgg ctc gga gac cag gac gcc atc cac tac atg acc aag gag         624
Ser Asp Trp Leu Gly Asp Gln Asp Ala Ile His Tyr Met Thr Lys Glu
            195                 200                 205 gcc ccc aag tcc att atc gag ctg gaa cac tac ggt gtt ccc ttc tct         672
Ala Pro Lys Ser Ile Ile Glu Leu Glu His Tyr Gly Val Pro Phe Ser
210                 215                 220 cga aac gac gag ggc cga atc tac cag cga gcc ttc ggt ggt cag tcc         720
Arg Asn Asp Glu Gly Arg Ile Tyr Gln Arg Ala Phe Gly Gly Gln Ser
225                 230                 235                 240 aag gac tac ggt aag gga ggc cag gcc tac cga acc tgt gcc gtt gcc         768
Lys Asp Tyr Gly Lys Gly Gly Gln Ala Tyr Arg Thr Cys Ala Val Ala
                245                 250                 255 gac cga acc ggc cac gcc atg ctg cac tct ctt tac gga cag tct ctc         816
Asp Arg Thr Gly His Ala Met Leu His Ser Leu Tyr Gly Gln Ser Leu
            260                 265                 270 cga cac aac act cac ttc ttt att gag tac ttc gcc atg gac ctg ctc         864
Arg His Asn Thr His Phe Phe Ile Glu Tyr Phe Ala Met Asp Leu Leu
            275                 280                 285 atg gag gac ggc gcc tgt gtc ggt gtc gtt gcc tac aac cag gag gac         912
Met Glu Asp Gly Ala Cys Val Gly Val Val Ala Tyr Asn Gln Glu Asp
    290                 295                 300 gga acc ctg cat cga ttc cga gcc cac aag acc gtt ctg gcc acc ggt         960
Gly Thr Leu His Arg Phe Arg Ala His Lys Thr Val Leu Ala Thr Gly
305                 310                 315                 320 ggt tac gga cga gcc tac ttc tcc tgt acc tct gcc cac acc tgt act        1008
Gly Tyr Gly Arg Ala Tyr Phe Ser Cys Thr Ser Ala His Thr Cys Thr
                325                 330                 335 ggt gac ggt atg gcc atg gtc acc cga gcc ggc ctt ccc ctc cag gat        1056
Gly Asp Gly Met Ala Met Val Thr Arg Ala Gly Leu Pro Leu Gln Asp
            340                 345                 350 ctg gag ttt gtc cag ttc cac cct acc ggt atc tat ggc tcc ggc tgt        1104
Leu Glu Phe Val Gln Phe His Pro Thr Gly Ile Tyr Gly Ser Gly Cys
            355                 360                 365
```

-continued

| | |
|---|---|
| ctg att act gag gga tcc cga ggt gag gga gga tac ctg ctc aac aag<br>Leu Ile Thr Glu Gly Ser Arg Gly Glu Gly Gly Tyr Leu Leu Asn Lys<br>370                             375                          380 | 1152 |
| aac ggt gag cga ttc atg gag cga tac gct ccc acc gcc aag gat ctg<br>Asn Gly Glu Arg Phe Met Glu Arg Tyr Ala Pro Thr Ala Lys Asp Leu<br>385                           390                         395                   400 | 1200 |
| gcc tcc cga gat gtc gtg tct cga tcc atg acc ctg gag atc cga gag<br>Ala Ser Arg Asp Val Val Ser Arg Ser Met Thr Leu Glu Ile Arg Glu<br>                         405                       410                       415 | 1248 |
| ggc cga ggt gtt ggc cag cac ggc gac cac atc ttc ctc cag ctg tcg<br>Gly Arg Gly Val Gly Gln His Gly Asp His Ile Phe Leu Gln Leu Ser<br>                   420                       425                     430 | 1296 |
| cat ctg ccc gcc tcc gtg ctc cac gag cga ctc ccc ggt att tcc gag<br>His Leu Pro Ala Ser Val Leu His Glu Arg Leu Pro Gly Ile Ser Glu<br>               435                       440                       445 | 1344 |
| acc gcc gcc att ttc gct ggt gtt gac gtt acc aag gag ccc atc ccc<br>Thr Ala Ala Ile Phe Ala Gly Val Asp Val Thr Lys Glu Pro Ile Pro<br>450                             455                       460 | 1392 |
| gtt ctc ccc acc gtt cac tac aac atg ggt ggt atc ccc acg cga tac<br>Val Leu Pro Thr Val His Tyr Asn Met Gly Gly Ile Pro Thr Arg Tyr<br>465                             470                       475                   480 | 1440 |
| acc ggt gag gtc ctt act cag gat gag aac ggt cag gac aag gtt gtc<br>Thr Gly Glu Val Leu Thr Gln Asp Glu Asn Gly Gln Asp Lys Val Val<br>                   485                       490                     495 | 1488 |
| gag ggt ctg ttc gcc tgt ggt gag gcc gcc tgt gtc tcc gtc cac ggt<br>Glu Gly Leu Phe Ala Cys Gly Glu Ala Ala Cys Val Ser Val His Gly<br>                       500                       505                     510 | 1536 |
| gcc aac cga ctt gga gcc aac tcc ctc gat ctg gtt gtc ttc ggc<br>Ala Asn Arg Leu Gly Ala Asn Ser Leu Leu Asp Leu Val Val Phe Gly<br>             515                       520                     525 | 1584 |
| cga gcc gtt gcc cac cga atc acc gag act ctt acc ccc ggt gct cct<br>Arg Ala Val Ala His Arg Ile Thr Glu Thr Leu Thr Pro Gly Ala Pro<br>530                             535                       540 | 1632 |
| ctt ccc cct gtc tct gct gac att ggt tac gag tcc att gct aac ctt<br>Leu Pro Pro Val Ser Ala Asp Ile Gly Tyr Glu Ser Ile Ala Asn Leu<br>545                           550                       555                   560 | 1680 |
| gac aag atg cga aac gcc gac ggt cct ctg tcc acc gct acc att cga<br>Asp Lys Met Arg Asn Ala Asp Gly Pro Leu Ser Thr Ala Thr Ile Arg<br>                   565                       570                     575 | 1728 |
| gac aag atg cag cga acc atg cag atg gat gtc tcc gtt ttc cga acc<br>Asp Lys Met Gln Arg Thr Met Gln Met Asp Val Ser Val Phe Arg Thr<br>                   580                       585                     590 | 1776 |
| cag gag tct ctt gag gat ggt gtc cga ggt atc act gct gtt gac cga<br>Gln Glu Ser Leu Glu Asp Gly Val Arg Gly Ile Thr Ala Val Asp Arg<br>             595                       600                     605 | 1824 |
| ctc att gac cag gtt ggt gtc acc gac cga tcc atg atc tgg aac act<br>Leu Ile Asp Gln Val Gly Val Thr Asp Arg Ser Met Ile Trp Asn Thr<br>610                             615                       620 | 1872 |
| gat ctt acc gag acc ctc gag ctg cag aac ctg ctc acc tgc gcc atg<br>Asp Leu Thr Glu Thr Leu Glu Leu Gln Asn Leu Leu Thr Cys Ala Met<br>625                             630                       635                   640 | 1920 |
| cag acc gcc tac tct gcc gtc gcc cga aag gag tct cga ggt gcc cat<br>Gln Thr Ala Tyr Ser Ala Val Ala Arg Lys Glu Ser Arg Gly Ala His<br>                   645                       650                     655 | 1968 |
| gcc cga gag gat tac ccc gac cga gac gat gtc aac tgg atg aag cat<br>Ala Arg Glu Asp Tyr Pro Asp Arg Asp Asp Val Asn Trp Met Lys His<br>                   660                       665                     670 | 2016 |
| acc ctc tcc tgg cag gat aag ccc ggt gac gag atc aag ctc ggc tac<br>Thr Leu Ser Trp Gln Asp Lys Pro Gly Asp Glu Ile Lys Leu Gly Tyr<br>675                             680                       685 | 2064 |

```
cga gcc gtc cag atg cac acc ctc gat gag tct gag tgt cct acc gtc    2112
Arg Ala Val Gln Met His Thr Leu Asp Glu Ser Glu Cys Pro Thr Val
    690             695                 700 cct ccc gcc aag cga gtc tac taa                                     2136
Pro Pro Ala Lys Arg Val Tyr
705                 710

<210> SEQ ID NO 2
<211> LENGTH: 711
<212> TYPE: PRT
<213> ORGANISM: Yarrowia lipolytica

<400> SEQUENCE: 2

Met Ser Asp Cys Leu Glu Asn Phe Ser Leu Ser Thr Ala Asp Ala Leu
1               5                   10                  15

Thr Val Tyr Pro His Asn Thr Pro Ser Asp Thr Thr Thr Ile Tyr
            20                  25                  30

Ser His Cys Gly Pro Leu Cys Ser Lys Ser Ser Arg Gln Leu Phe Ser
            35                  40                  45

Thr Tyr Arg Asn Thr Gln Asn Thr Ser Pro Pro His Asn Ala Cys Arg
    50                  55                  60

Lys Pro His Asn Thr Thr Asn Thr Glu Met Leu Arg Ala Ile Lys Asn
65                  70                  75                  80

Pro Arg Ala Val Leu Lys Ser Arg His Phe Ser Thr Ser Pro Val Val
                85                  90                  95

Ala Lys Val Phe Ala Asn Gly Pro Val Lys Ala Gln Glu Ala Pro Ser
            100                 105                 110

His Val Ala Ser Lys Tyr Ala Val Val Asp His Glu Tyr Asp Cys Val
            115                 120                 125

Val Val Gly Ala Gly Ala Gly Leu Arg Ala Ala Phe Gly Leu Ala
    130                 135                 140

Glu Ala Gly Phe Asn Thr Ala Cys Ile Ser Lys Leu Phe Pro Thr Arg
145                 150                 155                 160

Ser His Thr Val Ala Ala Gln Gly Gly Ile Asn Ala Ala Leu Gly Asn
                165                 170                 175

Met His Pro Asp Asn Trp Lys Trp His Met Tyr Asp Thr Val Lys Gly
            180                 185                 190

Ser Asp Trp Leu Gly Asp Gln Asp Ala Ile His Tyr Met Thr Lys Glu
            195                 200                 205

Ala Pro Lys Ser Ile Ile Glu Leu Glu His Tyr Gly Val Pro Phe Ser
    210                 215                 220

Arg Asn Asp Glu Gly Arg Ile Tyr Gln Arg Ala Phe Gly Gly Gln Ser
225                 230                 235                 240

Lys Asp Tyr Gly Lys Gly Gly Gln Ala Tyr Arg Thr Cys Ala Val Ala
                245                 250                 255

Asp Arg Thr Gly His Ala Met Leu His Ser Leu Tyr Gly Gln Ser Leu
            260                 265                 270

Arg His Asn Thr His Phe Phe Ile Glu Tyr Phe Ala Met Asp Leu Leu
    275                 280                 285

Met Glu Asp Gly Ala Cys Val Gly Val Ala Tyr Asn Gln Glu Asp
    290                 295                 300

Gly Thr Leu His Arg Phe Arg Ala His Lys Thr Val Leu Ala Thr Gly
305                 310                 315                 320

Gly Tyr Gly Arg Ala Tyr Phe Ser Cys Thr Ser Ala His Thr Cys Thr
                325                 330                 335

Gly Asp Gly Met Ala Met Val Thr Arg Ala Gly Leu Pro Leu Gln Asp
```

```
                340             345             350
Leu Glu Phe Val Gln Phe His Pro Thr Gly Ile Tyr Gly Ser Gly Cys
        355                 360                 365

Leu Ile Thr Glu Gly Ser Arg Gly Glu Gly Gly Tyr Leu Leu Asn Lys
    370                 375                 380

Asn Gly Glu Arg Phe Met Glu Arg Tyr Ala Pro Thr Ala Lys Asp Leu
385                 390                 395                 400

Ala Ser Arg Asp Val Val Ser Arg Ser Met Thr Leu Glu Ile Arg Glu
                405                 410                 415

Gly Arg Gly Val Gly Gln His Gly Asp His Ile Phe Leu Gln Leu Ser
                420                 425                 430

His Leu Pro Ala Ser Val Leu His Glu Arg Leu Pro Gly Ile Ser Glu
            435                 440                 445

Thr Ala Ala Ile Phe Ala Gly Val Asp Val Thr Lys Glu Pro Ile Pro
        450                 455                 460

Val Leu Pro Thr Val His Tyr Asn Met Gly Gly Ile Pro Thr Arg Tyr
465                 470                 475                 480

Thr Gly Glu Val Leu Thr Gln Asp Glu Asn Gly Gln Asp Lys Val Val
                485                 490                 495

Glu Gly Leu Phe Ala Cys Gly Glu Ala Ala Cys Val Ser Val His Gly
            500                 505                 510

Ala Asn Arg Leu Gly Ala Asn Ser Leu Leu Asp Leu Val Val Phe Gly
        515                 520                 525

Arg Ala Val Ala His Arg Ile Thr Glu Thr Leu Thr Pro Gly Ala Pro
    530                 535                 540

Leu Pro Pro Val Ser Ala Asp Ile Gly Tyr Glu Ser Ile Ala Asn Leu
545                 550                 555                 560

Asp Lys Met Arg Asn Ala Asp Gly Pro Leu Ser Thr Ala Thr Ile Arg
                565                 570                 575

Asp Lys Met Gln Arg Thr Met Gln Met Asp Val Ser Val Phe Arg Thr
            580                 585                 590

Gln Glu Ser Leu Glu Asp Gly Val Arg Gly Ile Thr Ala Val Asp Arg
        595                 600                 605

Leu Ile Asp Gln Val Gly Val Thr Asp Arg Ser Met Ile Trp Asn Thr
610                 615                 620

Asp Leu Thr Glu Thr Leu Glu Leu Gln Asn Leu Leu Thr Cys Ala Met
                625                 630                 635                 640

Gln Thr Ala Tyr Ser Ala Val Ala Arg Lys Glu Ser Arg Gly Ala His
            645                 650                 655

Ala Arg Glu Asp Tyr Pro Asp Arg Asp Val Asn Trp Met Lys His
        660                 665                 670

Thr Leu Ser Trp Gln Asp Lys Pro Gly Asp Glu Ile Lys Leu Gly Tyr
    675                 680                 685

Arg Ala Val Gln Met His Thr Leu Asp Glu Ser Glu Cys Pro Thr Val
                690                 695                 700

Pro Pro Ala Lys Arg Val Tyr
705                 710

<210> SEQ ID NO 3
<211> LENGTH: 807
<212> TYPE: DNA
<213> ORGANISM: Yarrowia lipolytica
<220> FEATURE:
<221> NAME/KEY: CDS
<222> LOCATION: (1)..(807)
```

<400> SEQUENCE: 3

```
atg ttc gcg ctc cga gcc tca aga aac gtt ctg aag agc cga ccc gtg      48
Met Phe Ala Leu Arg Ala Ser Arg Asn Val Leu Lys Ser Arg Pro Val
1               5                   10                  15 ttc gct cga ggc ctg gcc tcc acc gcc gag gcc cct aag gtg cct gcc      96
Phe Ala Arg Gly Leu Ala Ser Thr Ala Glu Ala Pro Lys Val Pro Ala
            20                  25                  30 ccc cga atc aag aag ttt ggc atc tac cga tgg aac cca gac acc ccc     144
Pro Arg Ile Lys Lys Phe Gly Ile Tyr Arg Trp Asn Pro Asp Thr Pro
        35                  40                  45 gaa aag aag ccc gag ctc aag gag tac gag gtc gac ctg tca cag tgt     192
Glu Lys Lys Pro Glu Leu Lys Glu Tyr Glu Val Asp Leu Ser Gln Cys
    50                  55                  60 ggc ccc atg gtg ctg gac gcg ctc atc aag atc aag aac gag cag gac     240
Gly Pro Met Val Leu Asp Ala Leu Ile Lys Ile Lys Asn Glu Gln Asp
65                  70                  75                  80 ccc acc ctg acg ttc cga cgg tcg tgc cga gag ggc atc tgt ggc tcc     288
Pro Thr Leu Thr Phe Arg Arg Ser Cys Arg Glu Gly Ile Cys Gly Ser
                85                  90                  95 tgt gcc atg aac att gag ggc cga aac acc ctc gca tgc ttg tgc cga     336
Cys Ala Met Asn Ile Glu Gly Arg Asn Thr Leu Ala Cys Leu Cys Arg
            100                 105                 110 atc aat ccc gac atc gcc aag gag gag aag atc tac cct ctg cct cac     384
Ile Asn Pro Asp Ile Ala Lys Glu Glu Lys Ile Tyr Pro Leu Pro His
        115                 120                 125 atg ttt gtc gtc cga gac ctt gtc cct gac ctg acc cag ttc tac aag     432
Met Phe Val Val Arg Asp Leu Val Pro Asp Leu Thr Gln Phe Tyr Lys
    130                 135                 140 caa tac aag tcc atc gag ccc tac ctg cag cga gac gag gtc cct gcc     480
Gln Tyr Lys Ser Ile Glu Pro Tyr Leu Gln Arg Asp Glu Val Pro Ala
145                 150                 155                 160 gac ggt aag gag aac ctg cag tcc att gct gac cga cga aag ctc gac     528
Asp Gly Lys Glu Asn Leu Gln Ser Ile Ala Asp Arg Arg Lys Leu Asp
                165                 170                 175 ggt ctc tac gag tgc att ctg tgc gcc tgc tgc tcc acc tcg tgc cct     576
Gly Leu Tyr Glu Cys Ile Leu Cys Ala Cys Cys Ser Thr Ser Cys Pro
            180                 185                 190 tcg tac tgg tgg aac cag cag gag tac ctg ggc ccc gct gtc ctc atg     624
Ser Tyr Trp Trp Asn Gln Gln Glu Tyr Leu Gly Pro Ala Val Leu Met
        195                 200                 205 cag gcc tac cga tgg atg att gac tct cga gac gag gcc acc gcc aag     672
Gln Ala Tyr Arg Trp Met Ile Asp Ser Arg Asp Glu Ala Thr Ala Lys
    210                 215                 220 cga cag cag atg ctc gag aac tcc atg tct ctg tac cga tgc cac acc     720
Arg Gln Gln Met Leu Glu Asn Ser Met Ser Leu Tyr Arg Cys His Thr
225                 230                 235                 240 att atg aac tgc gcc cga acc tgc ccc aag ggt ctc aac ccc ggt ctg     768
Ile Met Asn Cys Ala Arg Thr Cys Pro Lys Gly Leu Asn Pro Gly Leu
                245                 250                 255 gcc atc gcc aag atc aag cga tcc atg gct ttc gtt taa                 807
Ala Ile Ala Lys Ile Lys Arg Ser Met Ala Phe Val
            260                 265
```

<210> SEQ ID NO 4
<211> LENGTH: 268
<212> TYPE: PRT
<213> ORGANISM: Yarrowia lipolytica

<400> SEQUENCE: 4

```
Met Phe Ala Leu Arg Ala Ser Arg Asn Val Leu Lys Ser Arg Pro Val
1               5                   10                  15
```

```
Phe Ala Arg Gly Leu Ala Ser Thr Ala Glu Ala Pro Lys Val Pro Ala
             20                  25                  30

Pro Arg Ile Lys Lys Phe Gly Ile Tyr Arg Trp Asn Pro Asp Thr Pro
         35                  40                  45

Glu Lys Lys Pro Glu Leu Lys Glu Tyr Glu Val Asp Leu Ser Gln Cys
     50                  55                  60

Gly Pro Met Val Leu Asp Ala Leu Ile Lys Ile Lys Asn Glu Gln Asp
 65                  70                  75                  80

Pro Thr Leu Thr Phe Arg Arg Ser Cys Arg Glu Gly Ile Cys Gly Ser
                 85                  90                  95

Cys Ala Met Asn Ile Glu Gly Arg Asn Thr Leu Ala Cys Leu Cys Arg
            100                 105                 110

Ile Asn Pro Asp Ile Ala Lys Glu Glu Lys Ile Tyr Pro Leu Pro His
            115                 120                 125

Met Phe Val Val Arg Asp Leu Val Pro Asp Leu Thr Gln Phe Tyr Lys
        130                 135                 140

Gln Tyr Lys Ser Ile Glu Pro Tyr Leu Gln Arg Asp Glu Val Pro Ala
145                 150                 155                 160

Asp Gly Lys Glu Asn Leu Gln Ser Ile Ala Asp Arg Arg Lys Leu Asp
                165                 170                 175

Gly Leu Tyr Glu Cys Ile Leu Cys Ala Cys Cys Ser Thr Ser Cys Pro
            180                 185                 190

Ser Tyr Trp Trp Asn Gln Glu Tyr Leu Gly Pro Ala Val Leu Met
        195                 200                 205

Gln Ala Tyr Arg Trp Met Ile Asp Ser Arg Asp Glu Ala Thr Ala Lys
    210                 215                 220

Arg Gln Gln Met Leu Glu Asn Ser Met Ser Leu Tyr Arg Cys His Thr
225                 230                 235                 240

Ile Met Asn Cys Ala Arg Thr Cys Pro Lys Gly Leu Asn Pro Gly Leu
                245                 250                 255

Ala Ile Ala Lys Ile Lys Arg Ser Met Ala Phe Val
            260                 265

<210> SEQ ID NO 5
<211> LENGTH: 510
<212> TYPE: DNA
<213> ORGANISM: Yarrowia lipolytica
<220> FEATURE:
<221> NAME/KEY: CDS
<222> LOCATION: (1)..(510)

<400> SEQUENCE: 5 tgc acc tcc tgg aat aat act aac cca gtg gct cga cct tct ctc cga    48
Cys Thr Ser Trp Asn Asn Thr Asn Pro Val Ala Arg Pro Ser Leu Arg
 1               5                  10                  15 cag ggt cct ctt gcc gcc tac cga tgc ctc cag acc cag acc acc acc    96
Gln Gly Pro Leu Ala Ala Tyr Arg Cys Leu Gln Thr Gln Thr Thr Thr
             20                  25                  30 cct gcc gag gct ctg gac atc ctt aac aag cag cga gcc ctt cga ccc   144
Pro Ala Glu Ala Leu Asp Ile Leu Asn Lys Gln Arg Ala Leu Arg Pro
         35                  40                  45 acc tcc ccc cat ctc gac atc tac cag ccc cag ctg acc tgg tac ctt   192
Thr Ser Pro His Leu Asp Ile Tyr Gln Pro Gln Leu Thr Trp Tyr Leu
     50                  55                  60 tct ggt ctg cac cga gtc acc ggt gtc gct ctc ggt ggt gct ctc tac   240
Ser Gly Leu His Arg Val Thr Gly Val Ala Leu Gly Gly Ala Leu Tyr
 65                  70                  75                  80
```

```
gct ctg ctg tgc gct tac gcc gct ggc cct gct ctt ggc att cac att    288
Ala Leu Leu Cys Ala Tyr Ala Ala Gly Pro Ala Leu Gly Ile His Ile
            85                  90                  95 gac tct acc acc ctt gcc cac act ttc gcc gcc gtc ccc ctg gtt gcc    336
Asp Ser Thr Thr Leu Ala His Thr Phe Ala Ala Val Pro Leu Val Ala
            100                 105                 110 aag ctc ccc ctg aag gct ctc gtt gca ttc ccc ttc acc ttc cac gcc    384
Lys Leu Pro Leu Lys Ala Leu Val Ala Phe Pro Phe Thr Phe His Ala
            115                 120                 125 ttc aac ggt gtc cga cat ctt gtg tgg gat ttc acc aag gag ctg act    432
Phe Asn Gly Val Arg His Leu Val Trp Asp Phe Thr Lys Glu Leu Thr
            130                 135                 140 gtc aag ggt gtc tac cga acc ggt tac acc gtt ctc ggc ctc tct gtt    480
Val Lys Gly Val Tyr Arg Thr Gly Tyr Thr Val Leu Gly Leu Ser Val
145                 150                 155                 160 ctg tcc gct gct gtt ctc gct ttc att taa                            510
Leu Ser Ala Ala Val Leu Ala Phe Ile
            165
```

```
<210> SEQ ID NO 6
<211> LENGTH: 169
<212> TYPE: PRT
<213> ORGANISM: Yarrowia lipolytica

<400> SEQUENCE: 6

Cys Thr Ser Trp Asn Asn Thr Asn Pro Val Ala Arg Pro Ser Leu Arg
1               5                   10                  15

Gln Gly Pro Leu Ala Ala Tyr Arg Cys Leu Gln Thr Gln Thr Thr
            20                  25                  30

Pro Ala Glu Ala Leu Asp Ile Leu Asn Lys Gln Arg Ala Leu Arg Pro
            35                  40                  45

Thr Ser Pro His Leu Asp Ile Tyr Gln Pro Gln Leu Thr Trp Tyr Leu
50                  55                  60

Ser Gly Leu His Arg Val Thr Gly Val Ala Leu Gly Gly Ala Leu Tyr
65                  70                  75                  80

Ala Leu Leu Cys Ala Tyr Ala Ala Gly Pro Ala Leu Gly Ile His Ile
            85                  90                  95

Asp Ser Thr Thr Leu Ala His Thr Phe Ala Ala Val Pro Leu Val Ala
            100                 105                 110

Lys Leu Pro Leu Lys Ala Leu Val Ala Phe Pro Phe Thr Phe His Ala
            115                 120                 125

Phe Asn Gly Val Arg His Leu Val Trp Asp Phe Thr Lys Glu Leu Thr
            130                 135                 140

Val Lys Gly Val Tyr Arg Thr Gly Tyr Thr Val Leu Gly Leu Ser Val
145                 150                 155                 160

Leu Ser Ala Ala Val Leu Ala Phe Ile
            165
```

```
<210> SEQ ID NO 7
<211> LENGTH: 414
<212> TYPE: DNA
<213> ORGANISM: Yarrowia lipolytica
<220> FEATURE:
<221> NAME/KEY: CDS
<222> LOCATION: (1)..(414)

<400> SEQUENCE: 7 atg cga aac cac aag atg ttc ggc acc atc ccc cag cct ccc gga ggc    48
Met Arg Asn His Lys Met Phe Gly Thr Ile Pro Gln Pro Pro Gly Gly
1               5                   10                  15
```

```
att gtc ggc acc gtc aac gac gcc gcc ccc gtt ccc ccc gcc aac ccc      96
Ile Val Gly Thr Val Asn Asp Ala Ala Pro Val Pro Pro Ala Asn Pro
         20                  25                  30 acc aag ggc tcc tac cac tgg acc ttt gag cga atc ctt gtc gtc ggc     144
Thr Lys Gly Ser Tyr His Trp Thr Phe Glu Arg Ile Leu Val Val Gly
     35                  40                  45 ctc atc ccc atg acc gtg ctg ccc ttc gcc acc ggc tcc atc tcc ccc     192
Leu Ile Pro Met Thr Val Leu Pro Phe Ala Thr Gly Ser Ile Ser Pro
 50                  55                  60 gtt ctg gac gcc act ctc ggt gct act ctg atc cac tct cag ctt         240
Val Leu Asp Ala Thr Leu Gly Ala Thr Leu Leu Ile His Ser Gln Leu
 65                  70                  75                  80 ggt ttc gag tct tgc att acc gac tac atc ccc aag cga gtc tac ggc     288
Gly Phe Glu Ser Cys Ile Thr Asp Tyr Ile Pro Lys Arg Val Tyr Gly
                 85                  90                  95 tcc att cac aac tac gcc atg tac ctg ctg tac gga gga acc gtg gtt     336
Ser Ile His Asn Tyr Ala Met Tyr Leu Leu Tyr Gly Gly Thr Val Val
            100                 105                 110 ggt ctc tac ggt ctc tac aag ctc gag act gag gat gtc ggc ctc acc     384
Gly Leu Tyr Gly Leu Tyr Lys Leu Glu Thr Glu Asp Val Gly Leu Thr
        115                 120                 125 gga acc atc aag aag atc tgg aac gct taa                             414
Gly Thr Ile Lys Lys Ile Trp Asn Ala
    130                 135
```

<210> SEQ ID NO 8
<211> LENGTH: 137
<212> TYPE: PRT
<213> ORGANISM: Yarrowia lipolytica

<400> SEQUENCE: 8

```
Met Arg Asn His Lys Met Phe Gly Thr Ile Pro Gln Pro Pro Gly Gly
 1               5                  10                  15

Ile Val Gly Thr Val Asn Asp Ala Ala Pro Val Pro Pro Ala Asn Pro
             20                  25                  30

Thr Lys Gly Ser Tyr His Trp Thr Phe Glu Arg Ile Leu Val Val Gly
         35                  40                  45

Leu Ile Pro Met Thr Val Leu Pro Phe Ala Thr Gly Ser Ile Ser Pro
     50                  55                  60

Val Leu Asp Ala Thr Leu Gly Ala Thr Leu Leu Ile His Ser Gln Leu
 65                  70                  75                  80

Gly Phe Glu Ser Cys Ile Thr Asp Tyr Ile Pro Lys Arg Val Tyr Gly
                 85                  90                  95

Ser Ile His Asn Tyr Ala Met Tyr Leu Leu Tyr Gly Gly Thr Val Val
            100                 105                 110

Gly Leu Tyr Gly Leu Tyr Lys Leu Glu Thr Glu Asp Val Gly Leu Thr
        115                 120                 125

Gly Thr Ile Lys Lys Ile Trp Asn Ala
    130                 135
```

<210> SEQ ID NO 9
<211> LENGTH: 25
<212> TYPE: DNA
<213> ORGANISM: Artificial sequence
<220> FEATURE:
<223> OTHER INFORMATION: primer P1

<400> SEQUENCE: 9
atcgatcgac aaaggcctgt ttctc                                          25

<210> SEQ ID NO 10
<211> LENGTH: 20
<212> TYPE: DNA
<213> ORGANISM: Artificial sequence
<220> FEATURE:
<223> OTHER INFORMATION: primer P2

<400> SEQUENCE: 10 gagtataacct gtacagactg                                                    20

<210> SEQ ID NO 11
<211> LENGTH: 28
<212> TYPE: DNA
<213> ORGANISM: Artificial sequence
<220> FEATURE:
<223> OTHER INFORMATION: primer P3

<400> SEQUENCE: 11
cgctctagac gtattgcact tcctttcc                                             28

<210> SEQ ID NO 12
<211> LENGTH: 27
<212> TYPE: DNA
<213> ORGANISM: Artificial sequence
<220> FEATURE:
<223> OTHER INFORMATION: primer P4

<400> SEQUENCE: 12
ccctgcctag gcgaagacct tggccac                                              27

<210> SEQ ID NO 13
<211> LENGTH: 32
<212> TYPE: DNA
<213> ORGANISM: Artificial sequence
<220> FEATURE:
<223> OTHER INFORMATION: primer P5

<400> SEQUENCE: 13
aaggtcttcg cctaggcagg gaggtatcaa cg                                        32

<210> SEQ ID NO 14
<211> LENGTH: 30
<212> TYPE: DNA
<213> ORGANISM: Artificial sequence
<220> FEATURE:
<223> OTHER INFORMATION: primer P6

<400> SEQUENCE: 14
gcgaagctta acagatacta aatcatttgc                                           30

<210> SEQ ID NO 15
<211> LENGTH: 17
<212> TYPE: DNA
<213> ORGANISM: Artificial sequence
<220> FEATURE:
<223> OTHER INFORMATION: primer P7

<400> SEQUENCE: 15
ggacatggtg cgaatgg                                                         17

<210> SEQ ID NO 16
<211> LENGTH: 17
<212> TYPE: DNA
<213> ORGANISM: Artificial sequence
<220> FEATURE:
<223> OTHER INFORMATION: primer P8

<400> SEQUENCE: 16

```
caggaaacag ctatgac                                              17

<210> SEQ ID NO 17
<211> LENGTH: 20
<212> TYPE: DNA
<213> ORGANISM: Artificial sequence
<220> FEATURE:
<223> OTHER INFORMATION: primer P9

<400> SEQUENCE: 17
cctacaatga cagaatgctg                                           20

<210> SEQ ID NO 18
<211> LENGTH: 34
<212> TYPE: DNA
<213> ORGANISM: Artificial sequence
<220> FEATURE:
<223> OTHER INFORMATION: primer P10

<400> SEQUENCE: 18
gtttctcggc tagctacgtc cgtcatgacc aacc                           34

<210> SEQ ID NO 19
<211> LENGTH: 33
<212> TYPE: DNA
<213> ORGANISM: Artificial sequence
<220> FEATURE:
<223> OTHER INFORMATION: primer P11

<400> SEQUENCE: 19
ggacgtagct agccgagaaa cacaacaaca tgc                            33

<210> SEQ ID NO 20
<211> LENGTH: 34
<212> TYPE: DNA
<213> ORGANISM: Artificial sequence
<220> FEATURE:
<223> OTHER INFORMATION: primer P12

<400> SEQUENCE: 20
gtgtacatcc taggccagag agccattgac gttc                           34

<210> SEQ ID NO 21
<211> LENGTH: 36
<212> TYPE: DNA
<213> ORGANISM: Artificial sequence
<220> FEATURE:
<223> OTHER INFORMATION: primer P13

<400> SEQUENCE: 21
ctctctggcc taggatgtac actcttgtac atacag                         36

<210> SEQ ID NO 22
<211> LENGTH: 18
<212> TYPE: DNA
<213> ORGANISM: Artificial sequence
<220> FEATURE:
<223> OTHER INFORMATION: primer P14

<400> SEQUENCE: 22
cacgtgctct ctcgttgc                                             18

<210> SEQ ID NO 23
<211> LENGTH: 21
<212> TYPE: DNA
<213> ORGANISM: Artificial sequence
```

```
<220> FEATURE:
<223> OTHER INFORMATION: primer P15

<400> SEQUENCE: 23
actacaacct cagttcagtg g                                          21

<210> SEQ ID NO 24
<211> LENGTH: 19
<212> TYPE: DNA
<213> ORGANISM: Artificial sequence
<220> FEATURE:
<223> OTHER INFORMATION: primer P16

<400> SEQUENCE: 24
ctaagggcga ctctgagga                                             19
```